US00PP35529P2

(12) United States Plant Patent
Spil

(10) Patent No.: US PP35,529 P2
(45) Date of Patent: Dec. 5, 2023

(54) ***ECHINACEA* PLANT NAMED 'IFECSSWHIB'**

(50) Latin Name: *Echinacea hybrida*
Varietal Denomination: IFECSSWHIB

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 18/114,839

(22) Filed: Feb. 27, 2023

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
See application file for complete search history.

(56) References Cited

PUBLICATIONS

CPVO Application Consulation (version 4.9.13); citation for 'IFECSSWHIB'. Retrieved from the Internet on Jun. 20, 2023.*

* cited by examiner

*Primary Examiner* — Susan McCormick Ewoldt
(74) *Attorney, Agent, or Firm* — C. Anne Whealy

(57) ABSTRACT

A new and distinct cultivar of *Echinacea* plant named 'IFECSSWHIB', characterized by its relatively compact and upright plant habit; moderately vigorous to vigorous growth habit; freely branching habit; strong flowering stems; numerous single-type inflorescences with white-colored ray florets and bright yellow green-colored receptacle spines; and good garden performance.

2 Drawing Sheets

Figure 1:
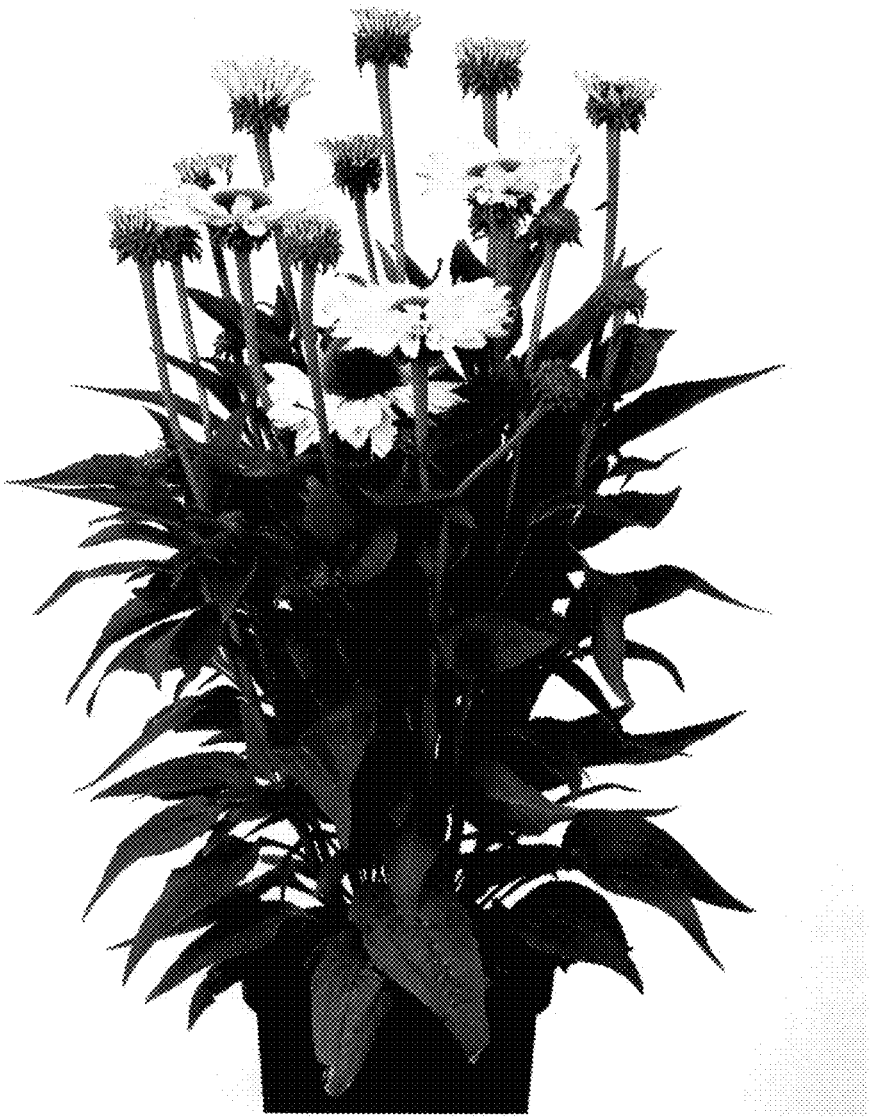

Botanical designation: *Echinacea hybrida.*
Cultivar denomination: 'IFECSSWHIB'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Innoflora Plant Breeding B.V. of Heerhugowaard, The Netherlands on Nov. 24, 2022, application number 2022/2660. Foreign priority is not claimed to this application.

BACKGROUND OF THE INVENTION

The present invention relates to a new and distinct cultivar of *Echinacea* plant, botanically known as *Echinacea hybrida,* and hereinafter referred to by the name 'IFECSSWHIB'.

The new *Echinacea* plant is a product of a planned breeding program conducted by the Inventor in Heerhugowaard, The Netherlands. The objective of the breeding program is to develop new vigorous and freely flowering *Echinacea* plants with large inflorescences with unique and attractive ray floret coloration.

The new *Echinacea* plant originated from an open-pollination in July, 2018 in Heerhugowaard, The Netherlands of a proprietary selection of *Echinacea hybrida* identified as code number 009-15-K001-02, not patented, as the female, or seed, parent with an unknown proprietary selection of *Echinacea hybrida,* as the male, or pollen, parent. The new *Echinacea* plant was discovered and selected by the Inventor as a single flowering plant from within the progeny of the stated open-pollination grown in a controlled greenhouse environment in Heerhugowaard, The Netherlands in August, 2019.

Asexual reproduction of the new *Echinacea* plant by in vitro meristem culture in a controlled environment in Heerhugowaard, The Netherlands since September, 2019 as shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'IFECSSWHIB'. These characteristics in combination distinguish 'IFECSSWHIB' as a new and distinct *Echinacea* plant:

1. Relatively compact and upright plant habit.
2. Moderately vigorous to vigorous growth habit.
3. Freely branching habit.
4. Strong flowering stems.
5. Numerous single-type inflorescences with white-colored ray florets and bright yellow green-colored receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are more compact than plants of the female parent selection.
2. Plants of the new *Echinacea* have stronger and healthier foliage than plants the female parent selection.
3. Inflorescences of plants of the new *Echinacea* have about three whorls of ray florets whereas inflorescences of plants of the female parent selection have two whorls of ray florets.

Plants of the new *Echinacea* can be compared to plants of *Echinacea purpurea* 'Virgin' disclosed in U.S. Plant Pat. No. 18,684. In side-by-side comparisons, plants of the new *Echinacea* differ primarily from plants of 'Virgin' in the following characteristics:

1. Plants of the new *Echinacea* are more compact than plants of 'Virgin'.
2. Plants of the new *Echinacea* flower later than plants of 'Virgin'.
3. Inflorescences of plants of the new *Echinacea* have about three whorls of ray florets whereas inflorescences of plants of 'Virgin' have a single whorl of ray florets.

Plants of the new *Echinacea* can also be compared to plants of *Echinacea purpurea* 'IFECSSWP', disclosed in U.S. Plant Pat. No. 34,455. In side-by-side comparisons, plants of the new *Echinacea* differ primarily from plants of 'IFECSSWP' in the following characteristics:

1. Plants of the new *Echinacea* are taller than plants of 'IFECSSWP'.
2. Plants of the new *Echinacea* have larger inflorescences than plants of 'IFECSSWP'.
3. Inflorescences of plants of the new *Echinacea* have about three whorls of ray florets whereas inflorescences of plants of 'IFECSSWP' have four whorls of ray florets.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet (FIG. 1) is a side perspective view of a typical flowering plant of 'IFECSSWHIB' grown in a container.

Figure 2:
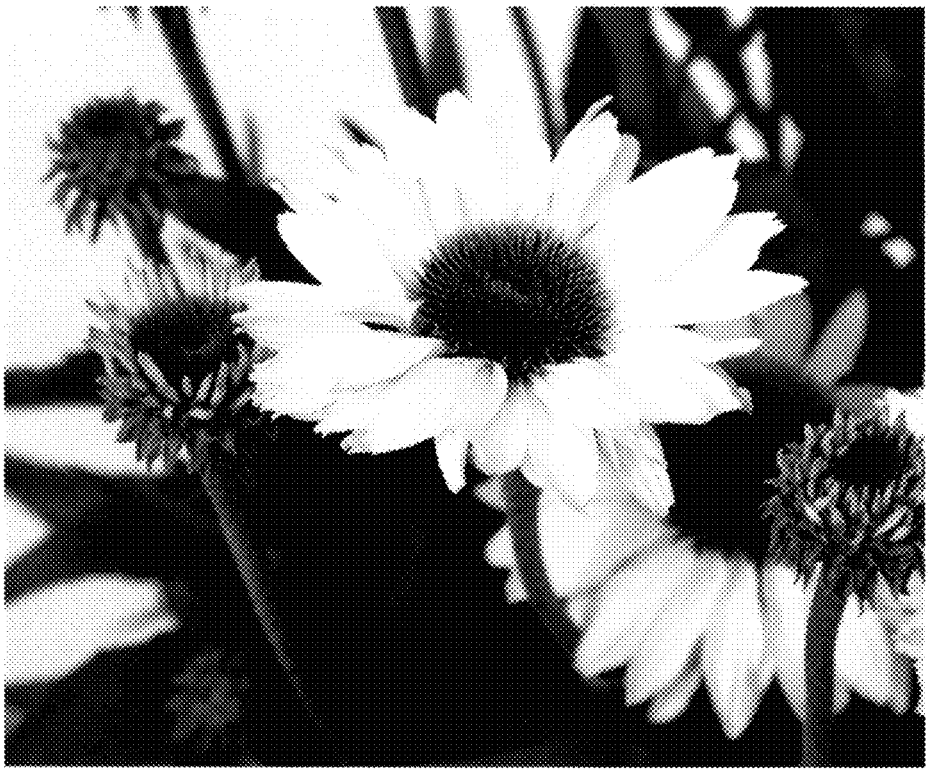

The photograph at the top of the second sheet (FIG. 2) is a close-up view of typical inflorescences of 'IFECSSWHIB'.

Figure 3:
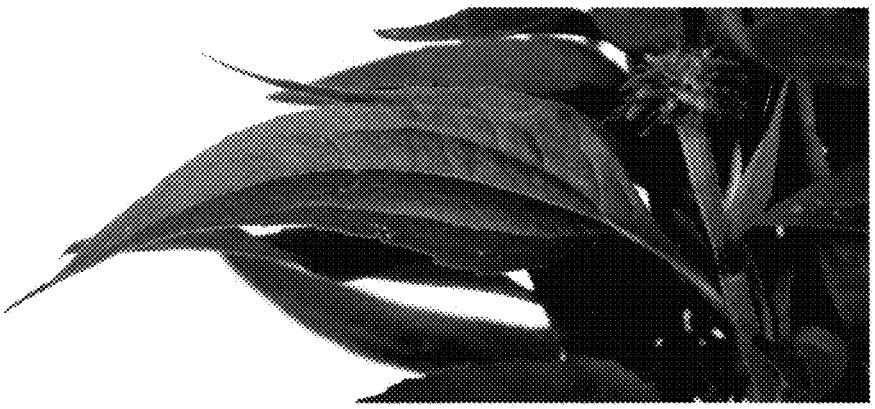

The photograph at the bottom of the second sheet (FIG. 3) is a close-up view of typical leaves of 'IFECSSWHIB'.

DETAILED BOTANICAL DESCRIPTION

The aforementioned photographs and following observations and measurements describe plants grown during the summer in 19-cm containers in an outdoor nursery in Heerhugowaard, The Netherlands and under cultural practices typically used in commercial *Echinacea* production. During the production of the plants, day temperatures ranged from 18 C to 34 C and night temperatures ranged from 8 C to 18 C. Plants were 16 weeks old when the photographs and description were taken. In the following description, color references are made to The Royal Horticultural Society Colour Chart, 2015 Edition, except where general terms of ordinary dictionary significance are used.

Botanical classification: *Echinacea hybrida* 'IFECSSWHIB'.

Parentage:

*Female parent*.—Proprietary selection of *Echinacea hybrida* identified as code number 009-15-K001-02, not patented.

*Male parent*.—Unknown proprietary selection of *Echinacea hybrida,* not patented.

Propagation:

*Type*.—By in vitro meristem culture.

*Time to initiate roots, summer*.—About twelve days at temperatures about 20 C.

*Time to initiate roots, winter*.—About 16 days at temperatures about 20 C.

*Time to produce a rooted young plant, summer*.—About 36 days at temperatures about 18 C.

*Time to produce a rooted young plant, winter*.—About 42 days at temperatures about 18 C.

*Root description*.—Thick, fleshy; typically white in color, actual color of the roots is dependent on substrate composition, water quality, fertilizer type and formulation, substrate temperature and physiological age of roots.

*Rooting habit*.—Moderately freely branching; sparse.

Plant description:

*Plant form and growth habit*.—Herbaceous perennial; relatively compact and upright plant habit; oblong in overall shape; freely basal branching habit with about eleven primary lateral branches and about 15 secondary lateral branches developing per plant; moderately vigorous to vigorous growth habit and moderate growth rate.

*Plant height*.—About 54.2 cm.

*Plant diameter or spread*.—About 44.2 cm.

*Lateral branches*.—Length: About 29.7 cm. Diameter: About 6 mm. Internode length: About 4 cm. Aspect: Erect to about 15 degrees from vertical. Strength: Strong. Texture: Moderately to densely pubescent; strigose. Color: Close to 144B with blotches, close to 143A.

Leaf description:

*Basal and cauline leaves*.—Arrangement: Alternate, simple. Length: About 12.9 cm. Width: About 5.3 cm. Shape: Ovate to narrowly ovate. Apex: Narrowly acute. Base: Short attenuate. Margin: Irregular and shallow indentations, or broadly dentate to shallow and coarsely serrate; mostly non-undulate to slightly and coarsely undulate. Texture and luster, upper surface: Moderately to densely pubescent, strigose and rough; slightly glossy. Texture and luster, lower surface: Moderately pubescent, strigose and rough; slightly glossy. Venation pattern: Pinnate. Color: Developing leaves, upper surface: Close to a blend of 137B and 146A. Developing leaves, lower surface: Close to 146B. Fully expanded leaves, upper surface: Close to 137A; venation, close to 144C. Fully expanded leaves, lower surface: Close to 147B; venation, close to 148C.

*Petioles, basal and cauline leaves*.—Length: About 6.6 cm. Diameter: About 2.5 mm by 4.5 mm. Texture, upper and lower surfaces: Sparsely pubescent. Color, upper surface: Close to 137B; midvein, close to 145B. Color, lower surface: Close to 138B; midvein, close to 146D.

Inflorescence description:

*Appearance*.—Single-type inflorescences with ray and disc florets arranged on a capitulum; inflorescences positioned upright above the foliar plane on mostly upright and strong peduncles.

*Flowering habit*.—Freely flowering habit with about 26 developing and fully developed inflorescences per plant.

*Fragrance*.—Moderately fragrant; sweet and pleasant.

*Time to flower*.—Plants flower continuously from late June into late September in The Netherlands.

*Inflorescence longevity*.—Inflorescences maintain good substance for about three weeks on the plant; inflorescences persistent.

*Inflorescence buds*.—Height: About 3.5 cm. Diameter: About 5.1 cm. Shape: Obovate with a flattened top. Color: Immature involucral bracts, close to 137B and NN137A; immature ray florets, close to 150D with apices, close to 144B to 144C; immature receptacle spines, close to 146A and 146B.

*Inflorescence size*.—Diameter: About 10.7 cm. Depth (height): About 4 cm. Disc diameter: About 3.8 cm.

*Receptacles*.—Height: About 1.4 cm. Diameter: About 1.4 cm. Shape: Broadly ovate. Color: Close to 156D and 157B.

*Ray florets*.—Quantity and arrangement: About 50 to 90 arranged in about three whorls at the base of the receptacle. Length: About 4.7 cm. Width: About 1.5 cm. Shape: Elliptic to narrowly obovate; slightly carinate. Apex: Emarginate to shallow praemorse. Base: Cuneate. Margin: Entire. Texture and luster, upper surface: Smooth, glabrous; moderately velvety; matte. Texture and luster, lower surface: Smooth, glabrous; slightly glossy. Aspect: About 22.5 degrees from horizontal. Color: When opening, upper surface: Close to 157D. When opening, lower surface: Close to 157C to 157D with apices, close to 145A. Fully opened, upper surface: Close to 155A; venation, close to 155A; color becoming closer to 157C with subsequent development. Fully opened, lower surface: Close to 155A and apices, close to 150A; venation, similar to lamina color; color becoming closer to 157C to 157D with venation and apices, close to 144B with subsequent development.

*Disc florets*.—Quantity and arrangement: About 400 per inflorescence, arranged spirally at the center of the inflorescence. Length: About 1.2 cm. Diameter: About 3.5 mm. Shape: Tubular; proximal 12.5% free, not fused. Apex: Acute. Base: Fused. Margin, free-part: Entire. Texture and luster, inner and outer surfaces: Smooth, glabrous; moderately glossy. Color, when opening, inner and outer surfaces: Apex: Close to 143B. Mid-section and base: Close to 145C. Color, fully opened, inner and outer surfaces: Apex: Close to 144B. Mid-section: Close to 145D. Base: Close to 150C.

*Receptacle spines*.—Quantity: One per disc floret; about 400 per inflorescence. Shape: Acicular. Apex: Acute. Base: Attenuate. Texture and luster: Smooth, glabrous; glossy. Color: Apex: Close to 145A. Mid-section: Close to 144A. Base: Close to 145D.

*Involucral bracts*.—Quantity per inflorescence: About 100 arranged in about four whorls. Length: About 1 cm. Width: About 3.5 mm. Shape: Narrowly ovate; moderately to strongly reflexed. Apex: Acute. Base: Cuneate. Margin: Entire. Texture and luster, upper surface: Smooth, glabrous; slightly glossy. Texture and luster, lower surface: Moderately pubescent; margins, densely pubescent; matte. Color, upper surface: Close to 137B; towards the apex and margins, close to NN137A. Color, lower surface: Close to 138B.

*Peduncles*.—Length: About 19.1 cm. Diameter: About 5 cm. Strength: Strong. Aspect: Mostly upright. Texture: Densely pubescent; strigose. Color: Close to 145A with blotches, close to 144A.

*Reproductive organs*.—Androecium (present on ray and disc florets): Quantity per floret: Five. Filament length: About 4 mm. Filament color: Close to 145C. Anther length: About 3.5 mm. Anther shape: Linear. Anther color: Close to a blend of N200A and 203A. Pollen amount: Moderate. Pollen color: Close to 21A. Gynoecium (present only on disc florets): Quantity per floret: One. Pistil length: About 7 mm. Stigma shape: Decurrent, unequal. Stigma color: Close to 152D. Style length: About 5.5 mm. Style color: Close to 145C. Ovary color: Close to 157C. Seeds and fruits: To date, seed and fruit development have not been observed on plants of the new *Echinacea*.

Pathogen & pest resistance: To date, plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35 C and to be hardy to USDA Hardiness Zones 3 to 4.

It is claimed:

1. A new and distinct *Echinacea* plant named 'IFECSS-WHIB' as illustrated and described.

* * * * *